United States Patent [19]
Sami et al.
[11] 4,400,393
[45] Aug. 23, 1983

[54] NOVEL BICYCLOOCTANE COMPOUNDS

[75] Inventors: Shunsuke Sami; Akihiko Sugie, both of Toyonaka; Keiichi Ono, Osaka; Hajime Kawakami; Atsuyuki Kojima, both of Takarazuka; Junki Katsube, Toyonaka, all of Japan

[73] Assignee: Sumitomo Chemical Company, Limited, Osaka, Japan

[21] Appl. No.: 246,938

[22] Filed: Mar. 24, 1981

[30] Foreign Application Priority Data

Apr. 11, 1980 [JP] Japan .................................. 55-48254

[51] Int. Cl.[3] .................... C07C 59/46; C07C 69/753; A01K 31/215

[52] U.S. Cl. ...................................... 424/305; 560/56; 560/100; 560/102; 560/107; 560/117; 560/256; 562/466; 562/499; 424/311; 424/317; 556/438; 549/420; 549/475

[58] Field of Search .............. 560/117, 256, 107, 100, 560/102, 56; 562/499, 466; 424/305, 317, 311; 556/438; 260/345.7 P, 345.8 P, 347.3, 347.4

[56] References Cited

FOREIGN PATENT DOCUMENTS 2013661 8/1979 United Kingdom ................ 560/119

*Primary Examiner*—Robert Gerstl
*Attorney, Agent, or Firm*—Stevens, Davis, Miller & Mosher

[57] ABSTRACT

A novel bicyclooctane derivative represented by the formula:

$CH(CH_2)_3CO_2R_1$ ... $Y_1O$ ... X ... $OY_2$ wherein $R_1$ is hydrogen or $C_{1\text{-}4}$alkyl, X is ethylene or vinylene, and $Y_1$ and $Y_2$ are independently hydrogen or a hydroxyl-protecting group, or a pharmaceutically acceptable salt of said compound in which $R_1$ is hydrogen. Said compound and pharmaceutically acceptable salt are chemically stable, have platelet anti-aggregation activity without undesirable pharmacological actions and exhibit the duration of high biological activity.

21 Claims, No Drawings

NOVEL BICYCLOOCTANE COMPOUNDS

The present invention relates to novel bicyclooctane compounds and to their production and use.

More particularly, this invention relates to novel bicyclooctane compounds, to a pharmaceutical composition containing at least one of the bicyclooctane compounds and to a process for the production thereof.

Compounds provided by this invention are representable by the following formula [I]:

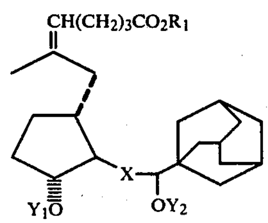

[I]

wherein $R_1$ is hydrogen or $C_{1-4}$ alkyl, X is ethylene or vinylene and $Y_1$ and $Y_2$ are each, independently of one another, hydrogen or a hydroxyl-protecting group, including a pharmaceutically acceptable salt of the compound (I) wherein $R_1$ is hydrogen.

In the significances as used above, "$C_{1-4}$ alkyl" means a straight or branched alkyl group having from one to four carbon atoms (e.g. methyl, ethyl, n-propyl, isopropyl, n-butyl), the hydroxyl-protecting group may be silyl (e.g. trialkylsilyl such as trimethylsilyl, dimethyl-tert-butylsilyl, dimethylisopropylsilyl, or dimethylethylsilyl), acetal (e.g. 2-tetrahydropyranyl, 2-tetrahydrofuranyl, 1-ethoxyethyl, 2-methoxy-2-propyl, or 2-methoxyethoxymethyl), alkyl or aralkyl (e.g. methyl or benzyl) and acyl (e.g. $C_2$–$C_6$ alkanoyl such as acetyl, propionyl, or pivaloyl, and aroyl such as benzoyl, p-phenylbenzoyl, naphthoyl, which may be optionally substituted).

The compound represented by the formula [I] wherein $R_1$ is hydrogen may be transformed to its pharmacologically acceptable salt form, which may be those of alkali or alkaline earth metals such as sodium, potassium, magnesium or calcium and those of ammonium or primary, secondary, tertiary or quaternary ammonium such as methylammonium, diethylammonium, piperidinium, tetraethylammonium or tris(hydroxymethyl)methylammonium.

Among the bicyclooctane compounds of the formula [I], the preferred compounds are those of the formula [I] in which $Y_1$ and $Y_2$ are each hydrogen.

Further, the more preferred compounds may be represented by the formula [II]:

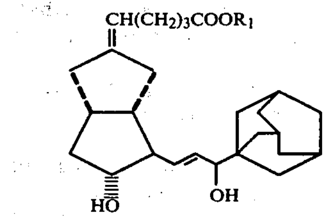

[II]

wherein $R_1$ is as defined above.

A tremendous amount of research in the synthetic organic chemistry, pharmacology and clinical medicine of prostaglandins has been performed since the discovery of prostaglandins.

In 1976, J. R. Vane et al. reported the isolation and biological effect of prostacyclin (prostaglandin $I_2$) [S. Moncada, R. Gryglewski, S. Bunting, and J. R. Vane, Nature (London), 263, 633 (1976)].

Prostaglandin $I_2$ [III], which is shown below, has several excellent pharmacological activities, for example, hypotensive, vasodilating, antiallergic, antiulcerogenic, and antithrombotic activities, and is expected to be useful in treating asthma, ulcer, thrombosis and hypertention.

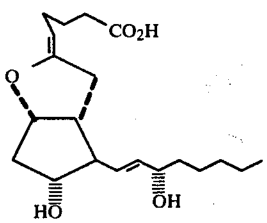

[III]

However, the short half-life of prostaglandin $I_2$ and its inseparable pharmacological actions complicate the potential value of this compound as a therapeutic agent.

As the result of a study to solve these problems, it has now been found that the novel bicyclooctane compounds [I] of the present invention and their pharmaceutically acceptable salts have potent platelet anti-aggregation activity without undesirable pharmacological actions and are useful in treating and preventing myocardial infractions, generally in treating and preventing thrombosis, and in treating diseases such as atherosclerosis, arteriosclerosis and hyperlipidemia.

In addition, the compounds [I] of this invention have a greater advantage in their chemical stability, and hence can be administered even orally, and furthermore exhibit the long duration of high biological activity.

The novel bicyclooctane compounds [I] and their pharmaceutically acceptable salts can effectively be administered orally in tablets, capsules, drops or syrups, or parenterally such as intravenously, subcutaneously, intramuscularly in sterile solutions or suspensions.

Doses in the range of about 1 mg to about 100 mg per kg of body weight per day are used, the exact dose depending on the age, weight and condition of the patient, and on the frequency and route of administration.

Accordingly, a basic object of the present invention is to provide novel and stable bicyclooctane compounds [I] having a selective antithrombotic activity.

Another object of this invention is to provide a process for producing those compounds [I]. These and other objects will be apparent to those skilled in the art to which the present invention pertains from the foregoing and subsequent descriptions.

The novel bicyclooctane compounds [I] of this invention can be prepared by the following methods:

Method (a): The novel bicyclooctane compounds of the formula [I]:

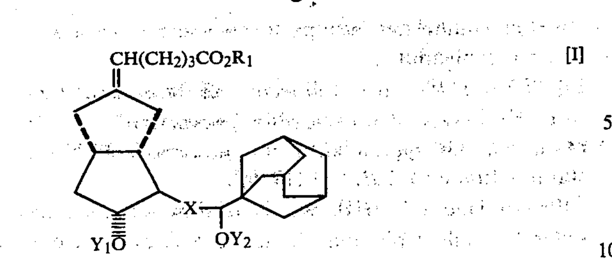

[I]

wherein $R_1$, $Y_1$, $Y_2$ and X are as defined above, can be prepared by reacting a carbonyl compound of the formula [IV]:

[IV]

wherein X is as defined above and $Y_3$ and $Y_4$ are each, independently of one another, hydrogen or a hydroxyl-protecting group such as silyl, acetal, alkyl or aralkyl, with a compound of the formula [V]:

$$(R_2)_3P{=}CH(CH_2)_3COOM \qquad [V]$$

wherein $R_2$ is aryl and M is an alkali metal and, if desired, followed by esterification of carboxyl group and/or protecting or deprotecting of hydroxyl or protected hydroxyl groups of the resulting product.

In the significances of the formula [V], M is an alkali metal such as sodium, lithium or potassium and is preferably sodium, and $R_2$ is preferably phenyl.

Method (b): The novel bicyclooctane compounds of the formula [VI]:

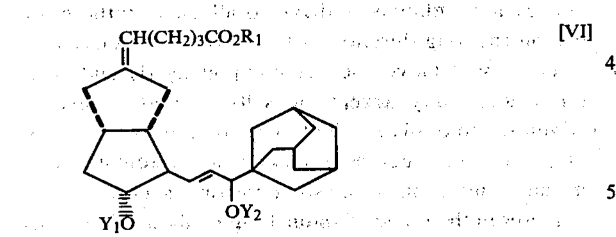

[VI]

wherein $R_1$, $Y_1$ and $Y_2$ are each as defined above, can be also prepared by reacting an aldehyde compound of the formula [VII]:

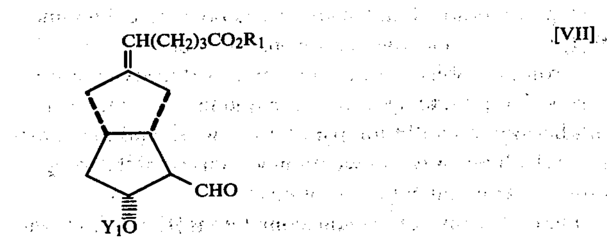

[VII]

wherein $R_1$ and $Y_1$ are each as defined above, with a compound of the formula [VIII]:

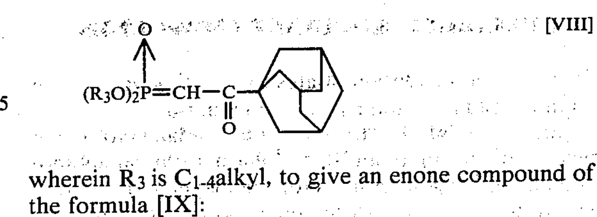

[VIII]

wherein $R_3$ is $C_{1-4}$alkyl, to give an enone compound of the formula [IX]:

[IX]

wherein $R_1$ and $Y_1$ are each as defined above, and further reducing the carbonyl group of the resulting enone [IX] with a reducing agent and, if desired, followed by esterification of the carboxyl group or hydrolysis of the ester group and/or protecting or deprotecting of hydroxyl or protected hydroxyl groups.

The Wittig reagents [V] and [VIII] can be prepared according to the known method [E. J. Corey et al., J. Amer. Chem. Soc., 91 5675 (1969)].

The Wittig reaction can be carried out in the presence of a solvent using 1–10 equivalents (preferably 2–6 equivalents) of the Wittig reagent [V] and [VIII]. Examples of the solvent are ethers (e.g. diethyl ether, tetrahydrofuran, dioxan, dimethoxyethane), hydrocarbons (e.g. benzene, toluene, hexane) and dimethylsulfoxide. The reaction can be controlled with warming or cooling depending upon the extent of the progress. The reaction time may vary depending upon the reaction temperature and the reagent to be used therein but it generally takes 1–24 hrs.

The carbonyl compound [IX] can be converted into the corresponding alcohol compound by reacting the former with a reducing agent in an inert solvent (e.g. diethyl ether, tetrahydrofuran, dimethoxyethane, pentane, hexane, benzene, toluene, methanol, ethanol) at a temperature ranging from −70° C. to room temperature.

For this reduction, there may be used any known reducing agent which can reduce only ketonic carbonyl group without affecting ester or acid groups or carbon-carbon double bonds.

Examples of such reducing agents are metal borohydrides (e.g. sodium borohydride, potassium borohydride, zinc borohydride, lithium triisobutylborohydride and sodium trimethoxyborohydride), lithium (tri-tert-butoxy)aluminum hydride, diisobutylaluminum hydride, diisobutylaluminum 2,6-di-tert-butyl-4-methylphenoxide, and aluminum alkoxides such as aluminum isopropoxide.

The reaction conditions may vary depending upon the reaction temperature and the reducing agent to be used therein.

The bicyclooctane compound thus obtained can be separated from the reaction mixture and purified by conventional procedures, and optionally followed by esterification or hydrolysis of carboxyl or ester group and/or protection or deprotection of hydroxyl or protected hydroxyl group.

The esterification or hydrolysis of carboxyl or ester group and/or the protection or deprotection of hydroxyl or protected hydroxyl group can be carried out by the conventional procedures [Protective Group in Organic Chemistry, edited by J. F. W. McOmie (1973), 95–143 and 183–215].

This invention further provides a pharmaceutical composition comprising at least one of the compounds of the formula [I] as an active ingredient and at least one pharmaceutically acceptable carrier or diluent.

For the preparation of pharmaceutical compositions, the compounds of the formula [I] may be mixed with conventional excipients, such as carriers, diluents, lubricants, fillers, binders, stabilizers or emulsifying agents, (e.g. lactose, sucrose, calcium phosphate, starch, talcum, casein, magnesium stearate, methyl cellulose, polyglycols, tragacanth and the like).

The resulting mixture may be processed in a usual manner to tablets, capsules, pills, ampoules and the like.

The starting materials of this invention can be prepared by the reactions and procedures described and examplified hereinafter. The bicyclooctane compound of formula [IV] is prepared by the sequence of transformations shown in Chart A and the bicyclooctane compound of the formula [VII] is prepared by the sequence of transformations shown in Chart B.

[Chart A]

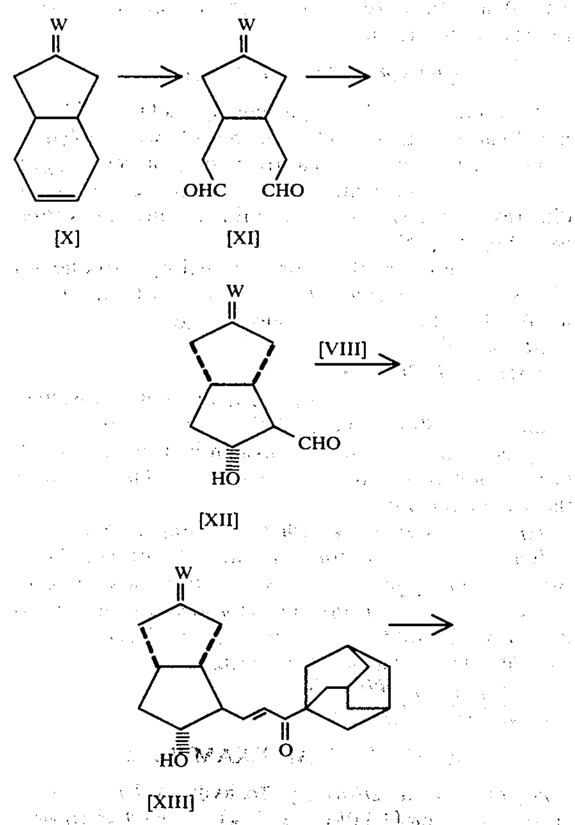

-continued

[Chart A]

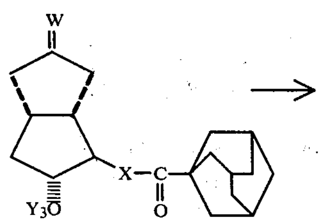

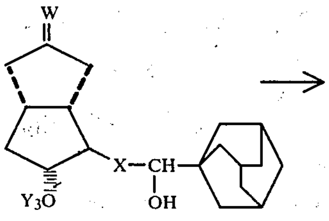

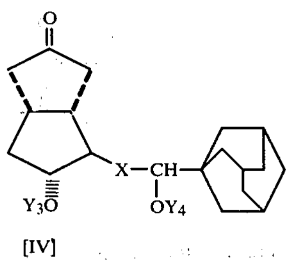

wherein X, $Y_3$ and $Y_4$ are each as defined above and W is a protected carbonyl group.

The aldol compound [XII] is effectively obtained from the cyclohexene compound [X] by oxidative cleavage to the dialdehyde compound [XI] followed by the intramolecular aldol reaction. [Japanese Patent Application Kokai (Laid-Open) No. 105,638/80].

the aldol compound [XII] thus obtained is converted by treatment with the Wittig reagent [VIII] to the enone compound [XIII] and if desired, followed by reduction of the double bond by conventional catalytic hydrogenation in the presence of palladium-on-carbon or similar catalyst and/or, if necessary, protection of the hydroxyl group to the compound of the formula [XIV].

Reduction of the carbonyl group of the compound [XIV] with a metal hydride reducing agent affords the compound [XV] and deprotection of the carbonyl-protecting group of the resulting compound [XV] and, if necessary, protection of the hydroxyl group before and/or after deprotection of the carbonyl-protecting group give the compound of the formula [IV].

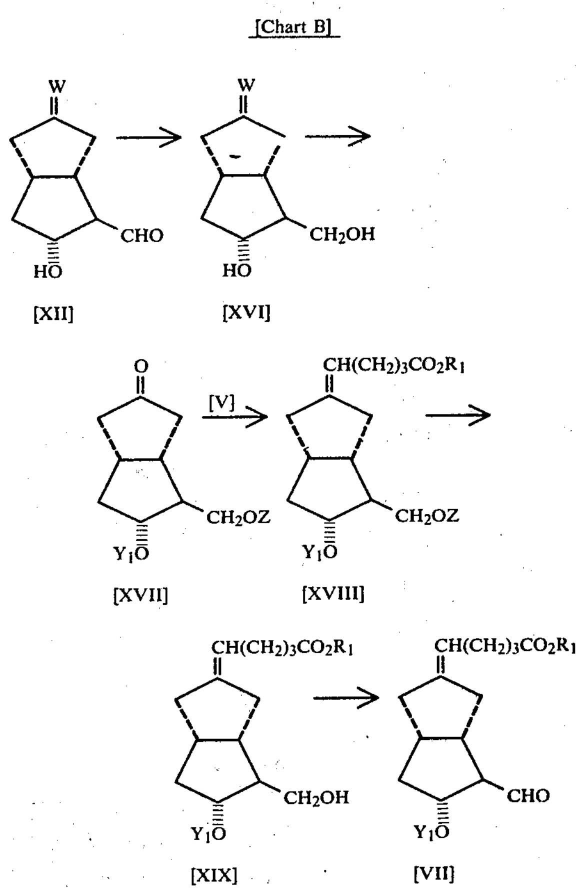

wherein $R_1$, W and $Y_1$ are each as defined above, Z is hydrogen or a hydroxyl-protecting group such as trityl which protects selectively a primary hydroxyl group.

The compound [XVI] is obtained from the aldol [XII] by metal hydride reduction. The compound [XVII] is obtained by deprotection of the carbonyl-protecting group of the compound [XVI], of which the primary hydroxyl group is selectively protected before or after deprotection of the carbonyl-protecting group and optionally followed by protection of the remaining secondary hydroxyl group.

The compound [XVII] is converted by the treatment with the Wittig reagent [V] to the carboxylic acid compound [XVIII], optionally followed by esterification and/or protection of the secondary hydroxyl group. The aldehyde compound [VII] is obtained by selective deprotection of the primary hydroxyl-protecting group of the compound [XVIII], followed by oxidation of the resulting alcoholic compound [XIX] with an oxidizing agent (e.g., Collins reagent, pyridinium chlorochromate, etc.).

Specific examples of the bicyclooctane compound [I] are as follows:

2β-[3'-(1-adamantyl)-3'-hydroxy-trans-1'-propenyl]-3α-hydroxy-7-(4''-carboxybutylidene)-cis-bicyclo[3,3,0]octane.

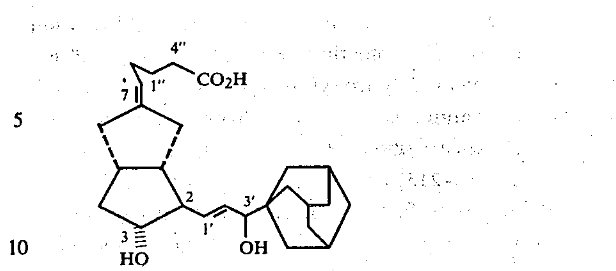

2β-[3'-(1-adamantyl)-3'-hydroxy-trans-1'-propenyl]-3α-hydroxy-7-(4''-methoxycarbonylbutylidene)-cis-bicyclo[3,3,0]octane.

2β-[3'-(1-adamantyl)-3'-hydroxypropyl]-3α-hydroxy-7-(4''-carboxybutylidene)-cis-bicyclo[3,3,0]octane.

2β-[3'-(1-admantyl)-3'-hydroxy-trans-1'-propenyl]-3α-acetoxy-7-(4''-methoxycarbonylbutylidene)-cis-bicyclo[3,3,0]octane.

2β-[3'-adamantyl)-3'-acetoxy-trans-1'-propenyl]-3α-acetoxy-7-(4''-methoxycarbonylbutylidene)-cis-bicyclo[3,3,0]octane.

2β-[3'-(1-adamantyl)-3'-acetoxy-trans-1'-propenyl]-3α-acetoxy-7-(4''-carboxybutylidene)-cis-bicyclo[3,3,0]octane.

According to the present invention, the bicyclooctane compound [I] can be obtained as a mixture of stereoisomers which can be easily separated by the conventional procedure (e.g. column chromatography, thin layer chromatography, etc.) with high purity.

The following Examples are given for the purpose of illustration of the preparation of starting materials embodying the invention in accordance with the above Charts (Referential Examples 1 to 8) and of the preparation of compounds embodying the invention (Examples 1 to 6), and they are not intended to limit the scope of the invention thereto.

REFERENTIAL EXAMPLE 1

A solution of 8,8-ethylenedioxy-cis-bicyclo[4,3,0]-non-3-ene (1.0 g) in methanol (50 ml) was cooled to −50° C. and subjected to a stream of ozonized oxygen. After the starting material was disappeared, 35 ml of dimethylsulfide was added and the mixture was stirred for 2 hrs at −15° C. to −5° C.

The mixture was then concentrated by introduction of a stream of nitrogen to give oily cis-1,2-diformylmethyl-4,4-ethylenedioxy-cyclopentane IR $\nu_{cm^{-1}}^{film}$: 1725.

NMR δ($CDCl_3$): 3.8, 9.7.

The dialdehyde (1.0 g) obtained above was dissolved in methanol (30 ml) and cooled at −15° C. to −5° C.

An aqueous solution of potassium hydroxide (5%, 10 ml) was added, and the mixture was stirred for 13 min at the same temperature.

To this mixture was added a saturated solution of sodium chloride and ethyl acetate. The organic layer was separated, washed with water, dried and concentrated under reduced pressure at a low temperature to give oily 2β-formyl-3α-hydroxy-7,7-ethylenedioxy-cis-bicyclo[3,3,0]octane as a main product.

IR $\nu_{cm^{-1}}^{film}$: 3400, 1710.

NMR δ($CDCl_3$): 3.85, 9.75.

REFERENTIAL EXAMPLE 2

A solution of 2β-formyl-3α-hydroxy-7,7-ethylenedioxy-cis-bicyclo[3,3,0]octane (7 g) in dry tetrahydrofuran (10 ml) was added at 3° C. under nitrogen to a tetrahydrofuran solution (150 ml) of the ylide prepared with dimethyl 2-oxo-2-(1-adamantyl)-ethylphosphonate (11 g) and sodium hydride (65%, 1.77 g). The mixture was stirred for 40 min at room temperature and poured into water and then extracted with diethyl ether. The extract was washed with aqueous sodium chloride solution, dried and concentrated in vacuo. The residue was chromatographed on silica gel to give 2β-[3'-(1-adamantyl)-3'-oxo-trans-1'-propenyl]-3α-hydroxy-7,7-ethylenedioxy-cis-bicyclo[3,3,0]octane.

IR $\nu_{cm^{-1}}^{film}$: 3450, 1680, 1620.

NMR δ($CDCl_3$): 7.0–6.5(2H, m), 3.9(4H, s), 3.5(1H, m).

REFERENTIAL EXAMPLE 3

An ethyl acetate solution (50 ml) of 2β-[3'-(1-adamantyl)-3'-oxo-trans-1'-propenyl]-3α-hydroxy-7,7-ethylenedioxy-cis-bicyclo[3,3,0]octane (1.1 g) was hydrogenated with 5% Pd-C under atmospheric pressure. The mixture was filtered to remove the catalyst, and the filtrate was concentrated to give oily 2β-[3'-(1-adamantyl)-3'-oxo-propyl]-3α-hydroxy-7,7-ethylenedioxy-cis-bicyclo[3,3,0]octane.

IR $\nu_{cm^{-1}}^{film}$: 3450, 1715.

NMR δ($CDCl_3$): 3.9(4H, s).

REFERENTIAL EXAMPLE 4

A methanolic solution (60 ml) of 2β-[3'-(1-adamantyl)-3'-oxo-trans-1'-propenyl]-3α-hydroxy-7,7-ethylenedioxy-cis-bicyclo[3,3,0]octane (3.3 g) was treated with sodium borohydride (1.2 g) with ice cooling.

Stirring was continued for 2 hrs and the excess reducing agent was quenched with acetone, and then the mixture was concentrated under reduced pressure. To the residue was added aqueous ammonium chloride, and the mixture was extracted with ethyl acetate.

The organic layer was dried and evaporated to give oily 2β-[3'-(1-adamantyl)-3'-hydroxy-trans-1'-propenyl]-3α-hydroxy-7,7-ethylenedioxy-cis-bicyclo[3,3,0]octane.

IR $\nu_{cm^{-1}}^{film}$: 3450, 2900.

The alcohol (3.3 g) obtained above was dissolved in a mixed solvent (30 ml) of acetic acid, water and tetrahydrofuran (3:1:1). The mixture was warmed at 45° C. and stirred for 2 hrs. The solvent was evaporated under reduced pressure and the residue was chromatographed on silica gel to give the more polar isomer, 2β-[3'-(1'-adamantyl)-3'α-hydroxy-trans-1'-propenyl]-3α-hydroxy-cis-bicyclo[3,3,0]octan-7-one and the less polar isomer, 2β-[3'-(1-adamantyl)-3'β-hydroxy-trans-1'-propenyl]-3α-hydroxy-cis-bicyclo[3,3,0]octan-7-one as a crystalline, respectively.

3'α-hydroxy isomer:

IR $\nu_{cm^{-1}}^{KBr}$: 3400, 2925, 1720.

NMR δ($CDCl_3$): 5.8–5.3(2H, m), 3.9(1H, m), 3.6(1H, m).

m.p. 137°–138° C.

3'β-hydroxy isomer:

IR $\nu_{cm^{-1}}^{KBr}$: 3450, 3400, 2925, 1720.

NMR δ($CDCl_3$): 5.8–5.5(2H, m), 4.0(1H, m), 3.6(1H, m).

m.p. 154°–155.5° C.

REFERENTIAL EXAMPLE 5

Following the procedures of Referential Example 4, there was obtained 2β-[3'-(1-adamantyl)-3'-hyroxypropyl]-3α-hydroxy-cis-bicyclo[3,3,0]octan-7-one from 2β-[3'-(1-adamantyl)-3'-oxo-propyl]-3α-hydroxy-7,7-ethylenedioxy-cis-bicyclo[3,3,0]octane (Referential Example 3)

IR $\nu_{cm^{-1}}^{film}$: 3400, 2930, 1735.

REFERENTIAL EXAMPLE 6

An ethanolic solution (300 ml) of 2β-formyl-3α-hydroxy-7,7-ethylenedioxy-cis-bicyclo[3,3,0]octane (10 g, obtained in Referential Example 1) was treated with sodium borohydride (10 g) at −10° C. to 0° C. under nitrogen. The mixture was stirred for 1 hr at the same temperature and aqueous ammonium chloride was added. After extraction with ethyl acetate, the extract was dried and concentrated in vacuo. The residue was dissolved in a mixed solvent of 10 ml of acetic acid and 10 ml of water and heated at 80° C. for 10 min. The mixture was concentrated in vacuo to give 2β-hydroxymethyl-3α-hydroxy-cis-bicyclo[3,3,0]octan-7-one.

Trityl chloride (11.3 g) was added to a pyridine solution (60 ml) of 2β-hydroxymethyl-3α-hydroxy-cis-bicyclo[3,3,0]octan-7-one (5.75 g). The mixture was stirred for 2.5 hrs at reflux and then poured into water and extracted with ethyl acetate. The extract was washed with water, dried and concentrated to oily 2β-trityloxymethyl-3α-hydroxy-cis-bicyclo[3,3,0]octan-7-one.

IR $\nu_{cm^{-1}}^{film}$: 3450, 2920, 1735, 1595.

A solution of sodium methylsulfinylmethide, prepared from 65% sodium hydride (1.6 g) and dimethylsulfoxide (21 ml), was cooled to 15° C.–20° C. and treated with 4-carboxybutyl triphenylphosphonium bromide (7.72 g) under nitrogen. The mixture was stirred for 10 min at 20° C.

To the above ylide solution was added a dimethylsulfoxide solution of 2β-trityloxymethyl-3α-hydroxy-cis-bicyclo[3,3,0]octan-7-one (2.41 g) obtained above at 20° C.–25° C. The reaction mixture was stirred for 21 hrs at room temperature and then poured into ice-water. The mixture was washed with diethyl ether and the aqueous layer was acidified with aqueous potassium bisulfate and extracted with ethyl acetate.

The ethyl acetate extract was washed with water, dried and concentrated in vacuo to give the residue, which was then chromatographed on silica gel to yield 2β-trityloxymethyl-3α-hydroxy-7-(4''-carboxybutylidene)-cis-bicyclo[3,3,0]octane.

IR $\nu_{cm^{-1}}^{film}$: 2950, 2550, 1720–1700.

NMR δ($CDCl_3$): 5.4–4.9(1H, br).

REFERENTIAL EXAMPLE 7

A diethyl ether solution of 2β-trityloxymethyl-3α-hydroxy-7-(4''-carboxybutylidene)-cis-bicyclo[3,3,0]octane (1.9 g) was treated with a diethyl ether solution of diazomethane.

The methyl ester thus obtained was dissolved in pyridine and acetic anhydride (5.2 g) was added. The mixture was stirred for 24 hrs at room temperature, then poured into ice-water, and extracted with ethyl acetate. The extract was dried and concentrated in vacuo to give oily 2β-trityloxymethyl-3α-acetoxy-7-(4''-methoxycarbonylbutylidene)-cis-bicyclo[3,3,0]octane.

IR $\nu_{cm^{-1}}^{film}$: 2925, 1740–1720, 1060.

NMR δ($CDCl_3$): 3.6(3H, s), 2.0(3H, s).

The ester compound (2.8 g) obtained above was dissolved in methyl acetate (90 ml) and cooled with ice-water. To this solution was added concentrated hydrochloric acid (9.0 g). The mixture was stirred for 20 min at the same temperature, and then neutralized with saturated sodium bicarbonate, extracted with ethyl acetate and dried. After evaporation of the solvent, the residue was chromatographed on silica gel to give oily 2β-hydroxymethyl-3α-acetoxy-7-(4''-methoxycarbonylbutylidene)-cis-bicyclo[3,3,0]octane.

IR $\nu_{cm^{-1}}^{film}$: 3450, 2925, 1730–1710.

NMR δ($CDCl_3$): 5.25(1H, br), 4.95(1H, m), 3.7(3H, s), 3.6(2H, d), 2.05(3H, s).

The alcohol compound (0.24 g) obtained above was dissolved in dichloromethane (20 ml) and 0.96 g of pyridinium chlorochromate. The mixture was stirred for 5 hrs at room temperature. To this mixture was added 200 ml of diethyl ether and stirred for a further 1 hr at the same temperature. After filtration of the undissolved material, the filtrate was concentrated to give oily 2β-formyl-3α-acetoxy-7-(4''-methoxycarbonylbutylidene)-cis-bicyclo[3,3,0]octane.

REFERENTIAL EXAMPLE 8

To a tetrahydrofuran (200 ml) solution of dimethyl methylphosphonate (20.2 g) was added a 1.6 M hexane solution of n-butyl lithium (100 ml) at −60° C. under nitrogen. To this mixture was added a THF solution of 1-adamantyl carboxylic acid chloride (30 g) and it was stirred at the same temperature for 5 hrs and at room temperature for 12 hrs. The mixture was diluted with water and extracted with diethyl ether. The extract was dried and concentrated in vacuo. After the residue was distilled off the volatile impurity (~200° C./0.6 mmHg), there was obtained dimethyl 2-oxo-2-(1-adamantyl)-ethylphosphonate as an oil.

EXAMPLE 1

A solution of sodium methylsulfinylmethide prepared from 65% sodium hydride (0.37 g) and dimethylsulfoxide (7.6 ml) was cooled to 15° C.–20° C. and treated with 4-carboxybutyl triphenylphoshonium bromide (3.47 g) under nitrogen.

The mixture was stirred for 10 min at 20° C., and to this solution was added a dimethylsulfoxide solution of 2β-[3'-(1-adamantyl)-3'α-hydroxy-trans-1'-propenyl]-3α-hydroxy-cis-bicyclo[3,3,0]octan-7-one (0.4 g, obtained in Referential Example 4) at 20° C.–25° C. The reaction mixture was stirred for 24 hrs at room temperature, and then diluted with water and 1 N aqueous sodium hydroxide.

The aqueous solution was washed with diethyl ether, acidified with 0.5 N aqueous potassium bisulfate and extracted with diethyl ether. The latter extract was dried and evaporated in vacuo. The residue was chromatographed on silica gel to give the more polar isomer 2β-[3'-(1-adamantyl)-3'α-hydroxy-trans-1'-propenyl]-3α-hydroxy-7-(4''-carboxy-1''E-butylidene)-cis-bicyclo[3,3,0]octane (E isomer) and the less polar isomer 2β-[3'-(1-adamantyl)-3'α-hydroxy-trans-1'-propenyl]-3α-hydroxy-7-(4''-carboxy-1''Z-butylidene)-cis-bicyclo[3,3,0]octane (Z isomer)

Z isomer:

IR $\nu_{cm^{-1}}^{film}$: 3350, 2600, 1700.

NMR δ($CD_3OD$): 5.6(2H, m), 5.3(1H, m), 3.8–3.5(2H, m).

E isomer:

IR $\nu_{cm^{-1}}^{film}$: 3400, 2600, 1700.

NMR δ($CDCl_3$): 5.5(2H, m), 5.3(1H, m), 3.8–3.5(2H, m).

EXAMPLE 2

Following the procedures of Example 1, there was obtained 2β-[3'-(1-adamantyl)-3'-hydroxypropyl]-3α-hydroxy-7-(4''-carboxybutylidene)-cis-bicyclo[3,3,0]octane IR $\nu_{cm^{-1}}^{film}$: 3400, 2600, 1700.

NMR δ($CDCl_3$): 5.3(1H, m), 3.8–3.5(2H, m).

EXAMPLE 3

A tetrahydrofuran (5 ml) solution of 2β-formyl-3α-acetoxy-7-(4''-methoxycarbonylbutylidene)-cis-bicyclo[3,3,0]octane (0.2 g, obtained in Referential Example 7) was added at 34° C. under nitrogen to a tetrahydrofuran solution (11 ml) of the ylide prepared with dimethyl 2-oxo-2-(1-adamantyl)ethylphosphonate (0.46 g) and sodium hydride (65%, 0.08 g). The mixture was stirred for 30 min at 30° C. and then poured into water and extracted with ethyl acetate. The extract was washed with water, dried and concentrated in vacuo. The residue was chromatographed on silica gel to give 2β-[3'-(1-adamantyl)-3'-oxo-trans-1'-propenyl]-3α-acetoxy-7-(4''-methoxycarbonylbutylidene)-cis-bicyclo[3,3,0]octane IR $\nu_{cm^{-1}}^{film}$: 2900, 1735, 1680, 1620.

NMR δ($CDCl_3$): 6.6(2H, m), 5.3(1H, m), 3.6(3H, s), 2.0(3H, s).

A methanolic solution (10 ml) of 2β-[3'-(1-adamantyl)-3'-oxo-trans-1'-propenyl]-3α-acetoxy-7-(4''-methoxycarbonylbutylidene)-cis-bicyclo[3,3,0]octane (70 mg) obtained above was treated with a chilled methanolic solution of sodium borohydride (25 mg) at 5° C., and stirred for 2 hrs at the same temperature. The excess reducing agent was quenched with acetone, and the mixture was concentrated in vacuo. To the residue was added aqueous ammonium chloride and the mixture was extracted with ethyl acetate. The extract was washed with water, dried and concentrated to give 2β-[3'-(1-adamantyl)-3'-hydroxy-trans-1'-propenyl]-3α-acetoxy-7-(4''-methoxycarbonylbutylidene)-cis-bicyclo[3,3,0]octane as an oil IR $\nu_{cm^{-1}}^{film}$: 3400, 2900, 1725.

NMR δ($CDCl_3$): 5.6(2H, m), 5.3(1H, m), 4.8(1H, m), 3.65(3H, s), 2.0(3H, s).

EXAMPLE 4

A mixture of 2β-[3'-(1-adamantyl)-3'-hydroxy-trans-1'-propenyl]-3α-acetoxy-7-(4''-methoxycarbonylbutylidene)-cis-bicyclo[3,3,0]octane (30 mg), sodium hydroxide (80 mg), 0.6 g of water and 0.6 ml of methanol was stirred for 70 min at room temperature. The mixture was diluted with water and washed with diethyl ether. The aqueous layer was acidified with 10% hydrochloric acid and extracted with ethyl acetate. The extract was washed with water, dried and concentrated in vacuo. The residue was chromatographed on silica gel to give 2β-[3'-(1-adamantyl)-3'-hydroxy-trans-1'-propenyl]-3α-hydroxy-7-(4''-carboxybutylidene)-cis-bicyclo[3,3,0]octane IR $\nu_{cm^{-1}}^{film}$: 3400, 2925, 2650, 1720–1700.

NMR δ($CDCl_3$): 5.5(2H, m), 5.3(1H, m), 3.7(2H, m).

EXAMPLE 5

Acetic anhydride (0.2 g) was added to a pyridine solution (5 ml) of 2β-[3'-(1-adamantyl)-3'-hydroxy-trans-1'-propenyl]-3α-acetoxy-7-(4''-methoxycarbonylbutylidene)-cis-bicyclo[3,3,0]octane (50 mg, obtained in Example 3). The mixture was stirred for 17 hrs at room temperature and then diluted with water and extracted with ethyl acetate. The extract was washed with water and concentrated in vacuo to give oily 2β-[3'-(1-adamantyl)-3'-acetoxy-trans-1'-propenyl]-3α-acetoxy-7-

(4''-methoxycarbonylbutylidene)-cis-bicyclo[3,3,0]octane

IR $\nu_{cm-1}^{film}$: 2925, 1730.

NMR δ($CDCl_3$): 5.6(2H, m), 5.3(2H, m), 4.8(1H, m), 3.65(3H, s), 2.05(3H, s), 2.0(3H, s).

EXAMPLE 6

To a mixture of 2β-[3'-(1-adamantyl)-3'α-hydroxy-trans-1'-propenyl]-3α-hydroxy-7-(4''-carboxy-1''E-butylidene)-cis-bicyclo[3,3,0]octane (30 mg, obtained in Example 1) and pyridine (2 ml) was added acetic anhydride (0.115 g). The mixture was stirred for 24 hrs at room temperature, then poured into water, and extracted with ethyl acetate. The extract was washed with water, dried and concentrated in vacuo to give 2β-[3'-(1-adamantyl)-3'α-acetoxy-trans-1'-propenyl]-3α-acetoxy-7-(4''-carboxy-1''E-butylidene)-cis-bicyclo[3,3,0]octane IR $\nu_{cm-1}^{film}$: 2600, 1730-1700, NMR δ($CDCl_3$): 5.5(2H, m), 5.3(2H, m), 4.8(1H, m), 2.05(3H, s), 2.0(3H, s).

What is claimed is:

1. A compound of the formula:

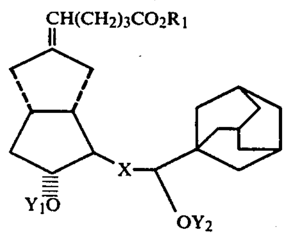

wherein $R_1$ is hydrogen or $C_1$–$C_4$ alkyl, X is ethylene or vinylene and $Y_1$ and $Y_2$ are each, independently of one another, hydrogen or a hydroxyl-protecting group selected from the group consisting of silyl, acetal, alkyl, aralkyl, $C_2$–$C_6$ alkanoyl, and aroyl; or a pharmaceutically acceptable salt of such a compound wherein $R_1$ is hydrogen.

2. The compound according to claim 1, wherein each of $Y_1$ and $Y_2$ is hydrogen.

3. The compound according to claim 1, wherein $Y_1$ and $Y_2$ are each selected from the group consisting of $C_2$–$C_6$ alkanoyl and aroyl, independently of one another.

4. The compound according to claim 3, wherein $Y_1$ and $Y_2$ are each $C_2$–$C_6$ alkanoyl independently of one another.

5. A compound of the formula:

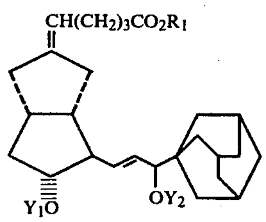

wherein $R_1$, $Y_1$ and $Y_2$ are each as defined in claim 1.

6. The compound according to claim 5, wherein each of $Y_1$ and $Y_2$ is hydrogen.

7. The compound according to claim 5, wherein $Y_1$ and $Y_2$ are each selected from the group consisting of $C_2$–$C_6$ alkanoyl and aroyl, independently of one another.

8. The compound according to claim 7, wherein $Y_1$ and $Y_2$ are each $C_2$–$C_6$ alkanoyl independently of one another.

9. 2β-[3'-(1-adamantyl)-3'α-hydroxy-trans-1'-propenyl]-3α-hydroxy-7-(4''-carboxy-1''E-butylidene)-cis-bicyclo[3,3,0]octane, and its stereoisomers (3'β and/or 1''Z).

10. 2β-[3'-(1-adamantyl)-3'α-hydroxy-trans-1'-propenyl]-3α-hydroxy-7-(4''-methoxycarbonyl-1''E-butylidene)-cis-bicyclo[3,3,0]octane, and its stereoisomers (3'β and/or 1''Z).

11. 2β-[3'-(1-adamantyl)-3'α-hydroxypropyl]-3α-hydroxy-7-(4''-carboxy-1''E-butylidene)-cis-bicyclo[3,3,0]octane, and its stereoisomers (3'β and/or 1''Z).

12. 2β-[3'-(1-adamantyl)-3'α-hydroxy-trans-1'-propenyl]-3α-acetoxy-7-(4''-methoxycarbonyl-1''E-butylidene)-cis-bicyclo[3,3,0]octane and its stereoisomers (3'β and/or 1''Z).

13. 2β-[3'-(1-adamantyl)-3'α-acetoxy-trans-1'-propenyl]-3α-acetoxy-7-(4''-methoxycarbonyl-1''E-butylidene)-cis-bicyclo[3,3,0]octane and its stereoisomers (3'β and/or 1''Z).

14. 2β-[3'-(1-adamantyl)-3'α-acetoxy-trans-1'-propentyl]-3α-acetoxy-7-(4''-carboxy-1''E-butylidene)-cis-bicyclo[3,3,0]octane and its stereoisomers (3'β and/or 1''Z).

15. A pharmaceutically acceptable salt of a compound as claimed in claim 1, wherein $R_1$ is hydrogen.

16. A pharmaceutical composition for the treatment or prevention of thrombosis comprising an anti-thrombotic effective amount of a compound as defined in claim 2 and a pharmaceutically acceptable carrier or diluent.

17. A process for treating or preventing thrombosis comprising administering to a patient an anti-thrombotic effective amount of a compound as defined in claim 2.

18. A compound according to claim 1 wherein $Y_1$ and $Y_2$ are selected from the group consisting of trimethylsilyl, dimethyl tert.-butylsilyl, dimethylisopropylsilyl, dimethylethylsilyl, 2-tetrahydropyranyl, 2-tetrahydrofuranyl, 1-ethoxyethyl, 2-methoxy-2-propyl, 2-methoxyethoxymethyl, methyl, benzyl, $C_2$–$C_6$ alkanoyl, benzoyl, p-phenyl benzoyl and naphthoyl.

19. A compound according to claim 3 wherein $Y_1$ and $Y_2$ are selected from the group consisting of $C_2$–$C_6$ alkanoyl, benzoyl, p-phenyl benzoyl and naphthoyl.

20. A compound according to claim 5 wherein $Y_1$ and $Y_2$ are selected from the group consisting of trimethylsilyl, dimethyl tert.-butylsilyl, dimethylisopropylsilyl, dimethylethylsilyl, 2-tetrahydropyranyl, 2-tetrahydrofuranyl, 1-ethoxyethyl, 2-methoxy-2-propyl, 2-methoxyethoxymethyl, methyl, benzyl, $C_2$–$C_6$ alkanoyl, benzoyl, p-phenyl benzoyl and naphthoyl.

21. A compound according to claim 7 wherein $Y_1$ and $Y_2$ are selected from the group consisting of $C_2$–$C_6$ alkanoyl, benzoyl, p-phenyl benzoyl and naphthoyl.

* * * * *